United States Patent
Gönczi et al.

(10) Patent No.: US 6,548,702 B1
(45) Date of Patent: Apr. 15, 2003

(54) METHOD FOR THE PREPARATION OF 2-METHOXY-4-(N-T-BUTYLAMINO-CARBONYL)-BENZENESULFONYL CHLORIDE

(75) Inventors: Csaba Gönczi, Budapest (HU); Éva Csikós, Budapest (HU); Félix Hajdú, Budapest (HU); István Hermecz, Budapest (HU); Gergely Héja, Szentendre (HU); Gergelyné Héja, Szentendre (HU); Lajos Nagy, Szentendre (HU); Andrea Sántáné Csutor, Budapest (HU); Kálmán Simon, Budapest (HU); Ágota Smelkóné Esek, Budapest (HU); Tiborné Szomor, Budapest (HU); Györgyné Szvoboda, Dunakeszi (HU)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/030,655

(22) PCT Filed: Jul. 13, 2000

(86) PCT No.: PCT/HU00/00080

§ 371 (c)(1),
(2), (4) Date: Apr. 26, 2002

(87) PCT Pub. No.: WO01/05754

PCT Pub. Date: Jan. 25, 2001

(30) Foreign Application Priority Data

Jul. 15, 1999 (HU) ............................................. 9902375

(51) Int. Cl.⁷ ..................... C07C 303/06; C07C 303/22; C07C 309/60; C07C 309/89
(52) U.S. Cl. ........................................ 564/142; 564/162
(58) Field of Search ................................... 564/142, 162

(56) References Cited

U.S. PATENT DOCUMENTS 3,953,507 A    4/1976  Baker et al.
5,994,350 A   11/1999  Foulon et al.

FOREIGN PATENT DOCUMENTS

WO    WO 97 15556 A    5/1997
WO    WO 98/25901   *  6/1998  ......... C07D/209/96

OTHER PUBLICATIONS

M.S. Shah; "4–Sulpho–3–hydroxybenzoic Acid"; Journal of the Chemical Society; 1930, pp 1293–1301.
S. Ramaswamy et al; "Phase–Transfer–Catalyzed Methylation of Hydroaromatic Acids, Hydroxyaromatic Aldehydes, and Aromatic Polycarboxylic Acids"; Environmental Science Technology, vol. 19, No. 6, 1985, pp 507–512.
Database Chemabs—Online; Chemical Abstracts Service, Columbus, Ohio, No. XP002153150 (1980) (Abstract).

* cited by examiner

Primary Examiner—Brian Davis
(74) Attorney, Agent, or Firm—Michael D. Alexander; Paul E. Dupont

(57) ABSTRACT

The invention relates to a process for the preparation of 2-methoxy-4-(N-t-butylaminocarbonyl)benzenesulfonyl chloride by sulfonating m-hydroxybenzoic acid, methylating the hydroxy group of the resulting sulfonic acid or its salt, transforming the carboxylic acid group and the sulfonic acid group to acid chloride groups and reacting the 4-chlorosulfonyl-3-methoxy-benzoyl chloride with t-butylamine, which comprises carrying out the sulfonation of the 3-methoxy-benzoic acid of general formula (II) with 96% sulfuric acid, separating the resulting 3-hydroxy-4-sulfobenzoic acid of general formula (III) in the form of its salt of general formula (IV), wherein Z stands for alkali metal or ammonium group, methylating the compound of general formula (IV) in the presence of a phase transfer catalyst at a pH value of about 11.5, transforming the 3-methoxy-4-sulfobenzoic acid mono salt of general formula (V), wherein the meaning of Z is as defined above, to the acid chloride of general formula (VI), and reacting the compound of general formula (VI) with t-butylamine used in equimolar amount or in a small excess, in the presence of an acid binding agent, in aprotic solvent, at low temperature.

19 Claims, 2 Drawing Sheets

I.

II.

III.

IV.

V.

VI.

METHOD FOR THE PREPARATION OF 2-METHOXY-4-(N-T-BUTYLAMINO-CARBONYL)-BENZENESULFONYL CHLORIDE

This application is a 371 of PCT HU00/00080 filed Jul. 13, 2000.

2-methoxy-4-(N-t-butylaminocarbonyl)benzenesulfonyl chloride is an important building block to the angiotensine antagonistic compound SR 121463. Its preparation is described in patent application WO 9715556. Because of the applied materials and reactions, the process described in the above patent application is appropriate to prepare the material only in laboratory scale, in low yield, and by involving several purification steps. The process is the following: it starts from 3-methoxy-4-nitrobenzoic acid, this is transformed via the acid chloride into the acylamide, the nitro group is then reduced and the amine group is exchanged in a Sandmeyer-type reaction, performed in acetic acidic medium using great excess of sulfur dioxide. The weakest part of the synthesis is the exchange of the amino group for chlorosulfonyl group. The reaction is difficult to control, the main reaction is accompanied by a series of side-reactions, thus a severely contaminated product is obtained in only about 50% yield.

Preparation of 2-methoxy-(4-aminocarbonyl) benzenesulfonamide and of 4-chlorosulfonyl-3-methoxybenzoyl chloride is known from the literature from the work of SHAH (J. Chem. Soc. 1930. 1293).

Our new process uses the basic elements of the above scientific work of 1930, but modifies it into a process, which can be technically realized and which widely satisfies the environmental, economical and technological requirements of the late 20th century.

Our process contains the following findings, compared to the method of SHAH: Sulfonation of the m-hydroxybenzoic acid is performed—instead of oleum, which is dangerous and difficult to treat—with 96% sulfuric acid, which also serves as he solvent of the reaction. After pouring the reaction mixture onto ice, the product is obtained as a precipitate which can be filtered off, which is pure, free of isomers. The yield of the reaction is around 90%. The sulfonic acid is isolated in the form of its potassium salt.

In the method described in the literature the methylation step was carried out using 18-fold excess of dimethyl sulfate, which was added in small portions subsequently with high amount of 25% potassium hydroxide. We have, however, found that even a small excess of dimethyl sulfate is sufficient if higher temperature is applied, the pH is maintained above 11.5 and a phase transfer catalyst (PTC) is used in aqueous medium or in a two-phase mixture. After isolating the product in the form of its salt, without further purification, a product of analytical purity (96–99%) can be obtained, in a yield as much as 90%.

Reacting the 3-methoxy-4-sulfobenzoic acid monopotassium salt with an inorganic acid halogenide the 4-chlorosulfonyl-3-methoxybenzoyl chloride is obtained. To our surprise we have found that at lower temperature, in an appropriate solvent the t-butylamine reacts selectively with the aromatic acid chloride. Thus, the desired 2-methoxy-4-(N-t-butylaminocarbonyl)benzenesulfonyl chloride is obtained in 92% yield, with a purity of 96%, so it can be used without further purification for the synthesis of drug substances.

In accordance with the above, the subject of our invention is a process for the preparation of 2-methoxy-4-(N-t-butylaminocarbonyl)benzenesulfonyl chloride by sulfonating m-hydroxybenzoic acid, methylating the hydroxy group of the resulting sulfonic acid or of its salt, transforming the carboxylic acid group and the sulfonic acid group into acid chloride groups and reacting the 4-chlorosulfonyl-3-methoxybenzoyl chloride with t-butylamine, which comprises carrying out the sulfonation of the 3-hydroxy-benzoic acid of the formula II

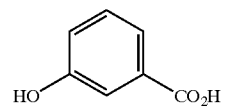

II.

with 96% sulfuric acid, separating the 3-hydroxy-4-sulfobenzoic acid of the formula III,

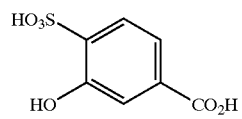

III.

thus obtained in the form of its salt of the general formula IV

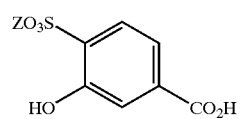

IV.

wherein Z stands for alkali metal or ammonium group-, methylating the compound of the general formula IV

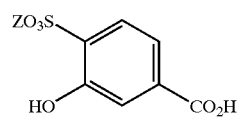

IV.

in the presence of a phase transfer catalyst at a pH above 11.5, transforming the 3-methoxy-4-sulfobenzoic acid mono salt of the general formula V

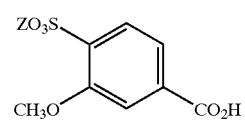

V.

wherein the meaning of Z is as defined above—to the acid chloride of the formula VI

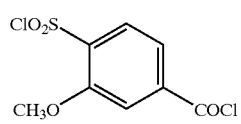

Figure 1:
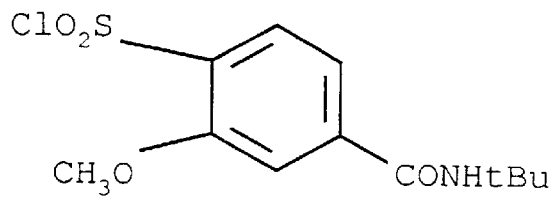
FIG. 1 shows the compounds of formulas I–IV and FIG. 2 shows the compounds of formulas V–VI.
Figure 1:
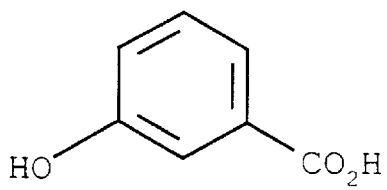
Figure 1:
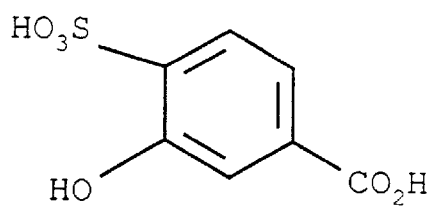
Figure 1:
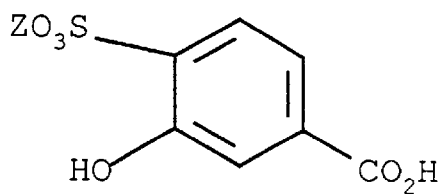
Figure 2:
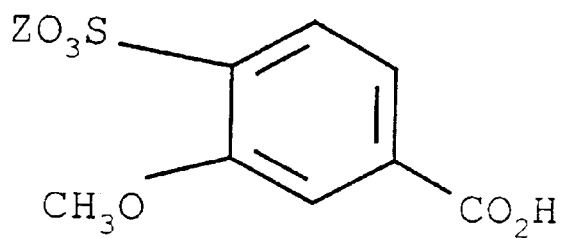
Figure 2:
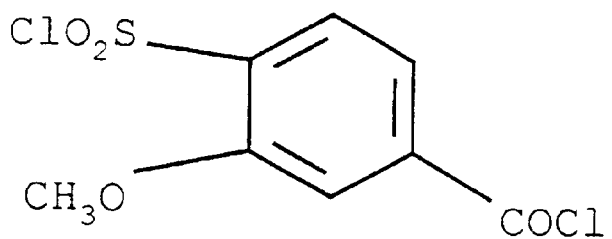

VI.

and reacting the compound of the formula VI thus obtained with t-butylamine, used in equimolar amount or in a small excess, in the presence of an acid binding agent, in aprotic solvent, at low temperature. (See "FIGS. 1 and 2").

According to a preferred embodiment of the invention the sulfonation is carried out with excess amount of 96% sulfuric acid, using the sulfuric acid also as the solvent of the reaction. The reaction is carried out at a temperature between 60° C. and 120° C., preferably at 90° C. The compound of the formula IV

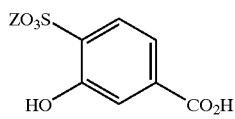

IV.

is separated in the form of its sodium, potassium or ammonium salt, preferably in the form of its potassium salt. As for phase transfer catalyst tetrabutylammonium hydroxide (TEBA) or trimethylbenzylammonium hydroxide or their salts, preferably tetrabutylammonium chloride or trimethylbenzylammonium chloride are used. Methylation of the compound of the general formula IV

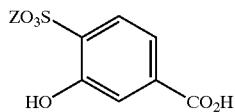

IV.

wherein the meaning of Z is the same as defined above—is carried out in water or in the mixture of water and a water-immiscible solvent. As for water-immiscible solvents toluene, xylene, or dichloromethane can be used. The compound of the general formula V

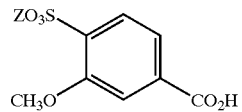

V.

is separated in the form of its sodium, potassium or ammonium salt, preferably in the form of its potassium salt.

As for acid binding agent trialkylamine, dialkylaniline, tertiary-alkylamine, preferably tert.-butylamine is used. As for an aprotic solvent chlorinated hydrocarbons, such as dichloromethane, dichloroethane, chloroform; or acetonitrile or acetone, preferably dichloromethane or acetone is used. The reaction of the 3-methoxy-4-chlorosulfonylbenzoyl chloride with t-butylamine is carried out at a temperature between −40° C. and room temperature, preferably between (−5)° C. and (−10)° C.

The invention is further demonstrated by the following examples, without limiting the claims to the examples.

EXAMPLES

Example 1

Into 550 g (300 cm$^3$) of 96% sulfuric acid 80 g (0.58 mol) of 3-hydroxybenzoic acid is added under stirring at room temperature. The resulting brown solution is heated to 90° C. and kept at that temperature. The thick, but treatable mass is poured onto crushed ice, the precipitate is filtered off, washed with ice-cold water. The wet product is dissolved in hot water, clarified with charcoal and its pH is adjusted to 3–3.5. After cooling the precipitated white crystals are filtered off, washed subsequently with water and acetone, and dried. 140g of 3-hydroxy-4-sulfobenzoic acid monopotassium salt monohydrate is obtained. It can be used without purification for the next step. Mp.: >300° C. Yield: 87.9%.

Example 2

To the solution of 11.2 g (0.2 mol) of potassium hydroxide in 50 cm$^3$ of distilled water 27.5 g (0.1 mol) of 3-hydroxy-4-sulfobenzoic acid potassium salt monohydrate is added and in that solution 0.5 g of TEBA is dissolved. The solution is heated to 50° C. and dropwise, under vigorous stirring to it the solution made of 25 cm$^3$ (33.25 g, 0.26 mol) of dimethyl sulfate, 17.4 g (0.31 mol) of potassium hydroxide and 60 cm$^3$ of water is added, while the pH is maintained between 11.5–12.5. The reaction mixture is kept at 50° C., and the pH is checked regularly. The solution is clarified with charcoal, filtered, the pH is adjusted to 2 with hydrochloric acid, then it is cooled in refrigerator overnight.

The precipitated crystals are filtered off, washed with distilled water and dried to constant weight: 26.7 g (92.7%).

Example 3a

To 105 cm$^3$ (172.7g, 1.128 mol) of phosphoryl chloride 57.6 g (0.2 mol) 3-methoxy-4-sulfobenzoic acid potassium salt monohydrate is added under stirring and the reaction mixture is heated to 110–120° C. from oil bath. Hydrogen chloride gas evolution ceases within 3 hours. The reaction is kept at that temperature for an additional 1 hour, then 500 g crushed ice is added to it. The precipitated white crystals are filtered off, washed with ice-cold water, dried in vacuum. 45–49 g of 3-methoxy-4-chlorosulfonylbenzoyl chloride is obtained. Mp.: 86–88° C., yield: 84–91%.

Example 3b

To 105 cm$^3$ (172.7g, 1.128 mol) of phosphoryl chloride 57.6 g (0.2 mol) of 3-methoxy-4-sulfobenzoic acid potassium salt monohydrate is added under stirring and the reaction mixture is heated to 110–120° C. from oil bath. Hydrogen chloride gas evolution ceases within 3 hours. The reaction is kept at that temperature for an additional 1 hour, then 500 g crushed ice is added to it. The reaction mixture is extracted several times with dichloromethane. The united organic phase is dried. After assay determination the solution is directly used for the next step.

Example 3c 137 g of dimethylformamide is cooled to −5° C., 235 g of phosphoryl chloride is added to it. The mixture is allowed to warm up then under stirring 125 g of 3-methoxy-4-sulfobenzoic acid is added to it in portions. It is then heated to 40–45° C., kept at that temperature for 1 hour, then poured onto 550 g of crushed ice. The precipitate is filtered off, washed thoroughly with water, and dried 110 g of product is obtained, its quality is similar to that of the product obtained in Example 3a.

Example 4

The dichloromethane solution of the 49 g (0.182 mol) 3-methoxy-4-chlorosulfonyl-benzoyl chloride—obtained as written in Example 3b—is cooled to −10° C., and to it dropwise, under vigorous stirring, in a period of 50–60 minutes, the −10° C. solution of 26.7 g (0.364 mol) of t-butylamine in 260 cm$^3$ of dichloromethane is added. The mixture is then poured onto 1000 cm$^3$ ice-water containing 40 cm³ of 1M hydrochloric acid. The dichloromethane phase is separated, washed with 2×1000 cm³ ice-water, dried over sodium sulfate, clarified with charcoal, filtered, and evaporated. 51.0 g of 2-methoxy-4-(N-t-butylaminocarbonyl) benzenesulfonyl chloride is obtained. Yield: 92%. Mp.: 145–149° C. Assay: 95–96% (by HPLC, NMR). Impurity: 1–3% di-t-butylamide derivative.

What is claimed is:

1. A process for the preparation of 2-methoxy-4-(N-t-butylaminocarbonyl)benzenesulfonyl chloride by sulfonating m-hydroxybenzoic acid, methylating the hydroxy group of the resulting sulfonic acid or its salt, transforming the carboxylic acid group and the sulfonic acid group to acid chloride groups and reacting the 4-chlorosulfonyl-3-methoxy-benzoyl chloride with t-butylamine, which comprises carrying out the sulfonation of the 3-hydroxy-benzoic acid of the formula II

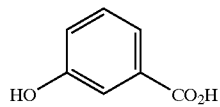

II with 96% sulfuric acid, separating the resulting 3-hydroxy-4-sulfobenzoic acid of the formula III

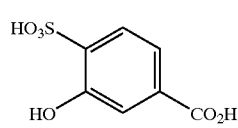

III in the form of its salt of the general formula IV, wherein Z stands for alkali metal or ammonium group-, methylating the compound of the general formula IV

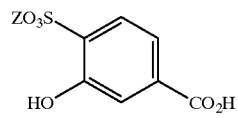

IV in the presence of a phase transfer catalyst at a pH value of about 11.5, transforming the 3-methoxy-4-sulfobenzoic acid mono salt of the general formula V

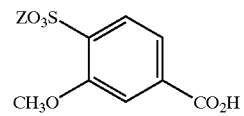

V wherein the meaning of Z is as defined above—to the acid chloride of the formula VI,

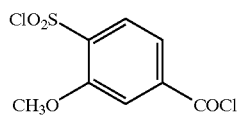

VI and reacting the compound of the formula VI with t-butylamine used in equimolar amount or in a small excess, in the presence of an acid binding agent, in aprotic solvent, at low temperature.

2. A process according to claim 1 which comprises carrying out the sulfonation reaction with excess amount of 96% sulfuric acid, using the sulfuric acid also as the solvent of the reaction.

3. A process according to claim 2 which comprises carrying out the reaction at a temperature between 60° C. and 120° C.

4. A process according to claim 1 which comprises separating the compound of the formula IV

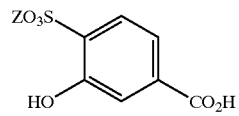

IV in the form of its sodium, potassium or ammonium salt.

5. A process according to claim 1 which comprises using as phase transfer catalyst tetrabutylammonium hydroxide or trimethylbenzylammonium hydroxide or the salts thereof.

6. A process according to claim 1 which comprises carrying out the methylation of the compound of the general formula IV

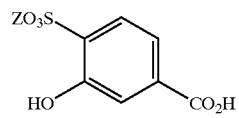

IV wherein the meaning of Z is as defined in claim 1 in water or in the mixture of water and a water-immiscible solvent.

7. A process according to claim 6 which comprises using as water-immiscible solvent toluene, xylene or dichloromethane.

8. A process according to claim 1 which comprises separating the compound of the general formula V

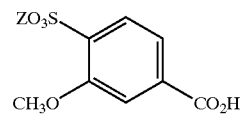

V in the form of its sodium, potassium or ammonium salt.

9. A process according to claim 1 which comprises using as acid binding agent trialkylamines, dialkylanilines, tertiary-alkylamines.

10. A process according to claim 1 which comprises using as aprotic solvent chlorinated hydrocarbons, acetonitrile or acetone.

11. A process according to claim 1 which comprises carrying out the reaction of 3-methoxy-4-chlorosulfonyl-benzoyl chloride with t-butylamine at a temperature between (−40)° C. and room temperature.

12. A process according to claim 3 which comprises carrying out the reaction at a temperature of 90° C.

13. A process according to claim 4 which comprises separating the compound of the formula IV in the form of its potassium salt.

14. A process according to claim 5 which comprises using a phase transfer catalyst tetrabutylammonium chloride or trimethylbenzylammonium chloride.

15. A process according to claim 8 which comprises separating the compound of the general formula V in the form of its potassium salt.

16. A process according to claim 9 which comprises using as the acid binding agent tert-butylamine.

17. A process according to claim 10 which comprises using as the aprotic solvent dichloromethane, dichloroethane, chloroform, acetonitrile or acetone.

18. A process according to claim 17 which comprises using as the aprotic solvent dichloromethane or acetone.

19. A process according to claim 11 which comprises carrying out the reaction of 3-methoxy-4-chlorosulfonylbenzoyl chloride with t-butylamine at a temperature between (−5)° C. and (−10)° C.

* * * * *